United States Patent [19]

Rasmussen et al.

[11] Patent Number: 4,874,822

[45] Date of Patent: Oct. 17, 1989

[54] PROCESS FOR THE ACRYLAMIDOACYLATION OF ALCOHOLS

[75] Inventors: Jerald K. Rasmussen; Steven M. Heilmann; Larry R. Krepski; Dean M. Moren, all of St. Paul, Minn.

[73] Assignee: Minnesota Mining and Manufacturing Company, St. Paul, Minn.

[21] Appl. No.: 178,507

[22] Filed: Apr. 7, 1988

[51] Int. Cl.$^4$ .................... C08F 8/30; C07C 102/00; C07C 103/133

[52] U.S. Cl. .................... 525/279; 560/172; 560/41; 560/125; 560/121; 560/123; 560/124; 556/419

[58] Field of Search ................ 525/279; 560/172, 41, 560/125, 121, 123, 124; 556/419

[56] References Cited

U.S. PATENT DOCUMENTS

| | | | |
|---|---|---|---|
| 4,485,236 | 11/1984 | Rasmussen et al. | 544/69 |
| 4,546,159 | 10/1985 | Taylor | 526/286 |
| 4,681,967 | 7/1987 | Green | 558/277 |
| 4,737,560 | 4/1988 | Heilmann et al. | 526/304 |
| 4,777,217 | 10/1988 | Rasmussen et al. | 527/312 |
| 4,777,276 | 10/1988 | Rasmussen et al. | 556/419 |

*Primary Examiner*—Joseph L. Schofer
*Assistant Examiner*—Thomas McDonald, Jr.
*Attorney, Agent, or Firm*—Donald M. Sell; Walter N. Kirn; Lorraine R. Sherman

[57] ABSTRACT

The present invention provides a dramatically improved process for the preparation of acrylamide and methacrylamide functional monomers, oligomers, and polymers that avoids the use of acidic catalysts which can cause undesired side reactions. The present invention process involves reacting an alkenyl azlactone with a hydroxy functional compound in the presence of a catalytic amount of either a bicyclic amidine or a trivalent phosphorus compound. These efficient basic catalysts provide unexpectedly increased reaction rates under mild conditions.

22 Claims, No Drawings

PROCESS FOR THE ACRYLAMIDOACYLATION OF ALCOHOLS

FIELD OF THE INVENTION

This invention relates to an improved process for the acrylamidoacylation of monomeric, oligomeric, and polymeric alcohols. The products of this process are useful as curable resins, for example, in coatings, films, binders, printing inks, adhesives, and the graphic arts.

BACKGROUND OF THE INVENTION

Free radically curable oligomers and polymers are well-known in the art, finding utility, for example, in the graphic arts, in the adhesives and coatings industry, and in a variety of biomedical areas. For the most part, these oligomers and polymers contain ethylenically unsaturated functional groups (often acrylate or methacrylate esters) at the termini of the polymer or pendant to the polymer chain. In general, these curable polymers are prepared from oligomers or polymers having various reactive functional groups and ethylenically unsaturated molecules having complementary reactive functional groups. Due to the wide variety of hydroxy functional oligomers and polymers which are available commercially, it is desirable to have efficient methods whereby these polymers can be converted into free radically curable polymers.

A method for the preparation of free radically curable oligomers which has advantages over prior art methods is taught in assignee's copending patent application U.S. Ser. No. 316,234 filed Oct. 29, 1981, and published European Patent Application No. 0 091 956, wherein acrylamide and methacrylamide functional oligomers are prepared by reaction of a nucleophilic group-substituted oligomer with an alkenyl azlactone. With hydroxy functional oligomers, this application exemplifies the use of certain Lewis acids e.g., aluminum chloride) as efficient catalysts for reaction with vinyl azlactones (e.g., 4,4 dimethyl-2-ethenyl-2-oxazolin-5-one). Although this process does allow the preparation of acrylamide functional oligomers, side reactions (leading to chain extension and in some cases crosslinking) can result in lower acrylamide functionality (i.e., higher acrylamide equivalent weight) than is theoretical. Correspondingly, assignee's copending patent application U.S. Ser. No. 019,473, filed Feb. 26, 1987, describes an improved process in which a hydroxy functional oligomer or polymer is reacted with an isopropenyl azlactone in the presence of an acidic catalyst. Utilization of an isopropenyl azlactone rather than a vinyl azlactone eliminates the troublesome side reactions.

Although the above described methods for the preparation of acrylamide and methacrylamide functional polymers are quite satisfactory in many instances, the acidic catalysts utilized can sometimes have detrimental effects. For instance, certain polymers are prone to hydrolysis, degradation, or chain scission in the presence of acids, thus leading to a reduction in molecular weight with a corresponding loss of physical properties. Other polymers may have functional groups which can interact preferentially with the acid catalysts, thereby reducing or destroying their catalytic activity.

U.S. Ser. No. 316,234 also teaches that hydroxy functional oligomers and alkenyl azlactones may be reacted in the presence of strong bases such as tetrabutylammonium hydroxide and alkali metal hydroxides and alkoxides. However, these very strong, nucleophilic hydroxide and alkoxide bases can also lead to hydrolysis and polymer degradation reactions. Furthermore, they are capable of preferential reaction with the alkenyl azlactones themselves, resulting in undesired side reactions. U.S. Pat. No. 4,546,159 recommends the use of 4-dialkylaminopyridines as basic catalysts for the reaction of alcohols with alkenyl azlactones. Although these catalysts are more efficient than other basic catalysts previously described in the art, they still provide relatively slow reaction rates.

In assignee's copending patent application U.S. Ser. No. 910,528, filed Sept. 23, 1986, several tertiary amine catalysts are recommended as being effective for the reaction of polyols and saturated azlactones. This reference recommends 1,8-diazabicyclo[5.4.0]undec-7-ene (DBU) and 1,5-diazabicyclo[4.3.0]non-5-ene (DBN) as the preferred catalysts.

U.S. Pat. No. 4,681,967 teaches a process for transesterification of a carboxylic or carbonic acid ester wherein the catalyst is either (a) a cyclic amidine (such a DBU or DBN), or (b) a Group V element-containing Lewis base and an epoxide. The Lewis base includes amidines, amines, and phosphines.

SUMMARY OF THE INVENTION

The present invention provides a dramatically improved process for the preparation of acrylamide and methacrylamide functional monomers, oligomers, and polymers that avoids the use of acidic catalysts which can cause undesired side reactions.

Briefly, the present invention process involves reacting an alkenyl azlactone with a hydroxy functional compound in the presence of a catalytic amount of either a bicyclic amidine or a trivalent phosphorus compound. These efficient basic catalysts provide unexpectedly increased reaction rates under mild conditions.

In this application:
"alkyl" means the monovalent group remaining after removal of a hydrogen atom from a linear, cyclic, or branched chain hydrocarbon containing 1 to 20 carbon atoms;
"lower alkyl" or "lower alkoxy" means $C_1$ to $C_4$ alkyl or alkoxy;
"aryl" means the monovalent group remaining after removal of one hydrogen atom from an aromatic or heteroaromatic compound (including aralkyl and alkaryl compounds) which can consist of one ring or two fused or catenated rings having 5 to 12 ring atoms which can include up to three ring heteroatoms selected from S, N, and O; this also includes substituted aromatics in which the substituents can be up to three halogen atoms and groups selected from lower alkyl, lower alkoxy, N,N-di(lower alkyl)amino, nitro, cyano, and lower alkyl carboxylic ester groups, and
"arenyl" means the monovalent group remaining after removal of a hydrogen from the alkyl portion of an organic compound containing both alkyl and aryl groups having 6 to 26 carbon and up to 3 S, N, and 0 heteroatoms.

DETAILED DESCRIPTION

This invention provides a method for the preparation of monomers, oligomers, and polymers which are characterized as having at least one acrylamide or methacrylamide functional group (hereinafter referred to collectively as acrylamide functional groups) per molecule, the method being accomplished by reaction of a hydroxy functional molecule of Formula I

wherein
R represents the residue of an organic molecule selected from monomer, oligomer, or polymer molecules to which the hydroxy groups are attached, the molecule having a valence of n and a number average molecular weight of up to 5,000,000; and
n is a positive integer of at least one and represents the valence of R; preferably n is an integer in the range of 1 to one million or more, with one to n equivalents of an alkenyl azlactone of general Formula II:

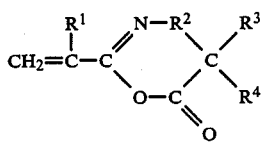

wherein
$R^1$ is hydrogen or methyl;
$R^2$ is a single bond or $R^2$ is a methylene group which can be substituted by one or two alkyl groups having 1 to 6 carbon atoms or a phenyl group; and
$R^3$ and $R^4$ are independently hydrogen, an alkyl group of 1 to 20 carbon atoms, a cycloalkyl group of 3 to 20 carbon atoms, an aryl group of 5 to 12 ring atoms, or an arenyl group of 6 to 26 carbon and heteroatoms, or $R^3$ and $R^4$ taken together with the carbon atom to which they are joined form a carbocyclic ring of 4 to 12 ring atoms in the presence of an effective amount of a catalyst selected from the group consisting of (a) bicyclic amidines, and (b) trivalent phosphorus compounds, to produce an acrylamide functional molecule having the general Formula III:

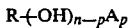

wherein
R and n are as defined above;
p is a positive integer between 1 and n inclusively; and
A is an acrylamide group having the formula

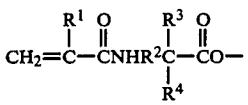

wherein $R^1$, $R^2$, $R^3$, and $R^4$ are as defined above.

The hydroxy functional molecules of Formula I which are useful in the practice of the invention may vary widely in terms of structure, chemical composition, molecular weight, provided that at least one hydroxy group per molecule is present for reaction with the azlactone of Formula II. Hydroxy functional molecules are well known in the art, and include a variety of monomeric, oligomeric, and polymeric alcohols. Representative monomeric alcohols include mono- and polyhydric alcohols such as methanol, ethanol, butanol, octanol, octadecanol, ethylene glycol, propylene glycol, 1,6-hexanediol, glycerol, trimethylolpropane, pentaerythritol, sorbitol, and the like. Representative oligomeric and polymeric alcohols include:

(a) Polyether polyols such as polyethyleneoxide and polypropyleneoxide based polyols (including the polyethoxylates of aliphatic alcohols and amines, alkyl phenols, and fatty acids and amides), polyethylenoxide/propyleneoxide copolymer polyols, and polytetramethyleneoxide based polyols;

(b) Polyester polyols, such as polycaprolactone polyols, polyneopentyladipate polyols, or other hydroxy functional polycarboxylic ester oligomers and polymers;

(c) Polysiloxane polyols such as those described in U.S. Pat. Nos. 4,098,742; 3,886,865; 3,577,264; and 4,013,698;

(d) Polycarbonate polyols such as the Duracarb TM series of polyols from PPG Industries Inc., Chicago, Ill.;

(e) Hydroxy functional polyacrylic and methacrylic ester polymers, such as those prepared according to U.S. Pat. Nos. 4,414,372; 4,417,034; 4,508,880, and 4,524,196;

(f) Phenolic resins, particularly the phenol/formaldehyde condensates referred to collectively as "resols", which contain —CH$_2$OH functionality;

(g) Polymers and copolymers of hydroxy functional vinyl monomers such as 2-hydroxyethyl acrylate, 2-hydroxyethyl methacrylate, hydroxypropyl acrylate, 2-hydroxyethyl acrylamide, 2-hydroxyethyl maleimide, 4-hydroxybutyl vinyl ether, glycerol monoacrylate or methacrylate, pentaerythritol monoacrylate, and diethyleneglycol monomethacrylate; these polymers include homopolymers of the hydroxy functional vinyl monomers as well as copolymers derived from copolymerization of the hydroxy functional vinyl monomers with one or more of a variety of comonomers. Suitable comonomers include essentially any free radically polymerizable ethylenically unsaturated monomers, examples of which include: the vinyl aromatic monomers such as styrene, α-methylstyrene, 2- and 4-vinyl pyridine, and the like; α,β-unsaturated carboxylic acids and their derivatives such as acrylic acid, methacrylic acid, itaconic acid, maleic acid, fumaric acid, crotonic acid, methyl methacrylate, butyl methacrylate, 2-ethylhexyl methacrylate, ethyl acrylate, butyl acrylate, iso-octyl acrylate, octadecyl acrylate, cyclhexyl acrylate, tetrahydrofurfuryl methacrylate, phenyl acrylate, phenethyl acrylate, benzyl methacrylate, β-cyanoethyl acrylate, maleic anhydride, diethyl itaconate, acrylamide, methacrylonitrile, N-butylacrylamide, and the like; vinyl esters of carboxylic acids such as vinyl acetate, vinyl 2-ethylhexanoate, and the like; vinyl halides such as vinyl chloride, vinylidene chloride, and the like; vinyl ethers such as ethyl vinyl ether, butyl vinyl ether, 2-ethylhexyl vinyl ether, and the like; olefins such as ethylene, N-vinyl compounds such as N-vinylpyrrolidone, N-vinylcarbazole, and the like; vinyl ketones such as methyl vinyl ketone and the like; and vinyl aldehydes such as acrolein, methacrolein, and the like;

(h) Polymers and copolymers derived from vinyl acetate, vinyl trifluoroacetate, or other vinyl esters, such as vinyl acetate/vinyl alcohol copolymers, polyvinyl alcohol, polyvinyl acetal, polyvinyl butyral, and other hydrolyzed or partially hydrolyzed vinyl ester copolymers;

(i) Cellulose and modified cellulose polymers such as cellulose acetate, cellulose nitrate, cellulose acetate propionate, cellulose acetate butyrate, cellulose acetate phthalate, hydroxypropyl cellulose, hydroxyethyl cellulose, benzyl cellulose, methyl cellulose, and ethyl cellulose; and (j) Phenoxy polymers, such as those prepared by step-growth polymerization of bisphenol A diglycidyl ether or other diepoxides with bisphenols.

The alkenyl azlactones of Formula II are also well known in the art, and include
4,4-dimethyl-2-ethenyl-2-oxazolin-5-one,
4,4-dimethyl-2-isopropenyl-2-oxazolin-5-one,
2-ethenyl-4-methyl-4-phenyl-2-oxazolin 5-one,
2-ethenyl-4,4-pentamethylene-2-oxazolin-5-one,
4,4-diphenyl-2-isopropenyl-2-oxazolin-5-one,
2-ethenyl-4-ethyl-4-methyl-2-oxazolin-5-one, and
4,4-dimethyl-2-ethenyl-4,5-dihydro-1,3-oxazin-6-one.

Others are disclosed in assignee's pending patent application U.S. Ser. No. 316,234, and in U.S. Pat. No. 4,304,705, incorporated herein by reference.

The catalysts which have been found to be unusually effective for the purposes of the invention are selected from the group consisting of:

(a) bicyclic amidines of the general structure IV:

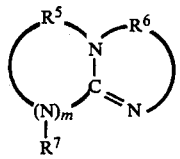

IV wherein $R^5$ and $R^6$ independently represent an alkylene group or an alkyl- or aryl-substituted alkylene group of 2 to 12 carbon atoms, $R^7$ is an alkyl or aryl group, and m is 0 or 1; and (b) trivalent phosphorus compounds, $R^8R^9R^{10}P$, wherein $R^8$, $R^9$, and $R^{10}$ are independently H, alkyl, aryl, arenyl, lower alkoxy, or lower dialkyl amino (2 to 8 C atoms).

Examples of amidines of Formula IV which are useful include 1,5-diazabicyclo[4.3.0]non-5-ene (DBN), 1,8-diazabicyclo[5.4.0]undec-7-ene (DBU), and 1,5,7-triazabicyclo[4.4.0]dec-5-ene (TBD). These compounds have the following structures:

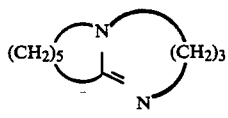

DBU

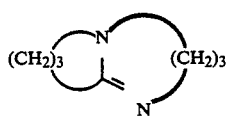

DBN

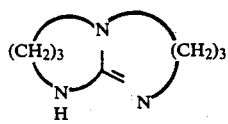

TBD

DBN and DBU are available from Aldrich Chemical Co., Milwaukee, Wis., and TBD is available from Fluka Chemical Corp., Ronkonkoma, N.Y. These and other amidines may be prepared by methods well known in the art, as described for example in H. Oediger, et al., Synthesis, 1972, 591. For example, DBU can be synthesized by cyanoethylation of caprolactam with acrylonitrile, reduction of the resultant N-(2-cyanoethyl)caprolactam to N-(3-aminopropyl)caprolactam, followed by cyclodehydration to the bicyclic amidine.

Examples of useful trivalent phosphorus compounds include trimethylphosphine, triethylphosphine, triethylphosphite, tributylphosphine, trioctylphosphine, tris(dimethylamino)phosphine, dimethylphenylphosphine, diphenylmethylphosphine diphenylphosphine, dipropylphosphine, 1,2-bis(di-n-propylphosphino)ethane, 1,3-bis(diphenylphosphino)propane, diethylmethoxyphosphine, and triphenylphosphine.

It is also envisioned as being within the scope of the invention to utilize polymer bound amidines and phosphines.

The amount of catalyst utilized in the instant process may vary from about 0.1 mole percent (based on azlactone) to about 50 mole percent or more. In most cases, however, 0.5 to 5 mole percent are sufficient to provide a reasonable reaction rate. The unusual effectiveness of the catalysts of the present process is not well understood. The fact that both stronger and weaker bases are less effective as catalysts indicates that factors other than base strength must be important. Also, whereas U.S. Ser. No. 910,528 teaches that bicyclic amidines such as DBU and DBN are quite effective catalysts for the reaction of alcohols with saturated azlactones, it was completely unexpected that these same catalysts would be an order of magnitude more effective (i.e. greater than ten times the reaction rate) for reactions with alkenyl azlactones. Even more surprising is the fact that the trivalent phosphorus catalysts are ineffective for catalysis of alcohol/saturated azlactone reactions.

The preferred conditions for carrying out the process of the invention are to mix the reactants and catalyst in the absence of solvent and to allow the reaction to proceed at room temperature (about 25° C.). These conditions, however, may be modified in certain instances as is clear to one skilled in the art. For example, reaction temperatures below (in the case of exothermic reactions) or above room temperature (for very slow reactions or in the case of solid reactants) may be advantageous. In general, reaction temperatures from about 0° C. to about 100° C. or so may be utilized to carry out the process of the instant invention. Also, in certain cases nonreactive solvents or diluents may be utilized to facilitate or mediate the reaction. By "nonreactive" is meant that the solvents do not contain functional groups which can react with either the azlactone, the hydroxy functional molecule, or the catalyst under the conditions utilized. Suitable nonreactive organic solvents include, for example, ethyl acetate, toluene, xylene, acetone, methyl ethyl ketone, acetonitrile, tetrahydrofuran, hexane, heptane, dimethylformamide, dimethylacetamide, and the like, or combinations thereof. In many instances, it may also be advantageous to add an effective amount of an antioxidant or free radical inhibitor (e.g. 0.00005 to 5.0 weight percent based on the combined weight of azlactone and hydroxy compound), such as a hindered phenol, to the reaction mixture or the final acrylamide functional product.

While in most instances it may be preferable to carry out the process of the invention so as to have a 1:1 stoichiometric balance of alkenyl azlactone to hydroxy functional groups, thus converting all of the hydroxy groups into acrylamide groups, it is also considered to be within the scope of the invention to utilize more or less than an equivalent amount of azlactone based upon the hydroxy equivalent weight, so long as enough azlactone is utilized to convert at least one hydroxy group on the average per molecule of Formula I to an acrylamide group.

As should be obvious to one skilled in the art, the reaction time required to convert the hydroxy functional compounds of Formula I to the acrylamide functional compounds of Formula III will vary widely. Reaction times will depend upon several factors, including the nature of the alcohol of Formula I, the substituents of the azlactone, the type of catalyst used, the amount of catalyst, the concentration of reactants and the temperature of the reaction. Progress of the reaction of the alkenyl azlactone with the hydroxy functional molecule is readily monitored by infrared spectroscopy by following the disappearance of the azlactone carbonyl stretching absorption near 1800 cm$^{-1}$ (about 5.5 micrometers). The absence of competing side reactions and estimation of acrylamide equivalent weights may be determined conveniently by $^1$H-NMR analysis.

Curing of the acrylamide and methacrylamide functional monomers, oligomers, and polymers can be accomplished thermally or utilizing actinic radiation, optionally in the presence of a free radical photoinitiator, by employing procedures well known in the art.

As should be obvious to one skilled in the art, the compounds of Formula III, prepared according to the instant process, being free radically curable or polymerizable by virtue of their acrylamide functionality, have widespread utility. Representative uses of the materials include, but are not limited to, components in coatings, films, adhesives, binders, resists, and the like. A review of more important applications can be found in G. E. Green, et al., *J. Macro. Sci.-Revs. Macro. Chem.*, 1981-1982, C21, 187-273.

The objects and advantages of the invention are further illustrated by the following examples, but the particular materials and amounts thereof recited in these examples, as well as other conditions and details, should not be construed to unduly limit this invention. Viscosities were obtained with a Brookfield Rheolog recording viscometer. Refractive indices were measured at 30° C. with a Baush & Lomb Abbe 3L refractometer equipped with a Sargeant-Welch circulating constant temperature bath.

EXAMPLE 1

Polycaprolactone polyol (Niax TM PCP TM 0300 from Union Carbide Corporation, OH equivalent weight 175) (10.00 g, 0.057 equiv), 2-vinyl-4,4-dimethylazlactone (VDM) (7.97 g, 0.057 mol), and DBN (0.15 g, 0.0012 mol, 2 mol % based on VDM charge) were mixed in a dry reaction vessel. An exothermic reaction ensued which was mediated by means of a cold water bath. The reaction was allowed to continue for two hours, at which time infrared and NMR analysis indicated complete conversion to the acrylamide functional compound.

EXAMPLES 2-10

Various alcohols and polyols were reacted with VDM under conditions similar to those of Example 1 to produce acrylamide functional materials. Starting materials and some properties of the final products are listed in Table I.

TABLE I

Acrylamide Functional Compounds

| Example | Alcohol | OH equiv. wt | Refractive Index (30° C.) | Viscosity (Poise) (30° C.) |
|---|---|---|---|---|
| 2 | (PCP 0300)* | 175 | 1.4859 | 135 |
| 3 | (Surfonic TM N10)[b] | 255 | 1.5102 | 1720 |
| 4 | (Surfonic N60)[b] | 440 | 1.4989 | 35.2 |
| 5 | (Surfonic N102)[b] | 620 | 1.4928 | 15.8 |
| 6 | (Surfonic N150)[b c] | 775 | 1.4877 | 11.4 |
| 7 | (Polypropyleneglycol)[a] | 190 | 1.4731 | 225 |
| 8 | (Carbowax TM 600)[c d] | 290 | 1.4835 | 96.5 |
| 9 | (PolyTMEG 650)[a e] | 300 | 1.4685 | 3.3 |
| 10 | (NIAX PCP 0210)[c g] | 390 | 1.4730[f] | 13.8[f] |

[a]2,6-ditertbutyl-4-methylphenol (BHT), 0.2% based on total weight, added as an antioxidant and polymerization inhibitor.
[b]Surfonic TM is the tradename of the series of monohydroxyfunctional surfactants from Texaco Chemical Co., Bellaire, TX, having the chemical structure C$_9$H$_{19}$C$_6$H$_4$(OCH$_2$CH$_2$)$_n$OH.
[c]Melted before being mixed with VDM and DBN.
[d]Carbowax is the tradename of Union Carbide Corporation for polyethyleneglycol, approximate average m. wt. 600.
[e]Polytetramethyleneglycol.
[f]Determined at 50° C.
[g]PCP 0210 is a polycaprolactone diol, a product of Union Carbide Corporation, Tarrytown, NY.

The data of Table I show that a wide variety of mono-and polyols are useful in the process of the invention.

EXAMPLES 11-17

A series of polycaprolactone polyols, the Placcel TM series, molecular wts in the range of 550 to 4,000, available from Daicel Chemical Industries, Ltd., Tokyo, Japan, were reacted with 0.5 stoichiometric equivalent of VDM using DBN as catalyst by a method similar to that of Example 1. Results are listed in Table 2.

TABLE 2

Polycaprolactone Acrylamides

| Example | Placcel | OH Equiv. wt. | Refractive index 30° C. | Refractive index 50° C. | Viscosity (Poise) 30° C. | Viscosity (Poise) 50° C. |
|---|---|---|---|---|---|---|
| 11 | 205 | 261 | 1.4761 | 1.4693 | 16.3 | 4.2 |
| 12 | 305 | 184 | 1.4850 | 1.4782 | 298 | 40 |
| 13 | 208[a] | 406 | — | 1.4680 | — | 7.0 |
| 14 | 212[a] | 615 | — | 1.4678 | — | 9.3 |
| 15 | 220[a] | 995 | — | 1.4670 | — | 18.7 |
| 16 | 230[a] | 1481 | — | 1.4650 | — | 24.4 |
| 17 | 240[a] | 1965 | — | 1.4650 | — | 52.8 |

[a]Polyol melted before mixing with VDM and DBN.

EXAMPLE 18

Examples 11-17 were repeated, this time using a full equivalent of VDM per hydroxy group, and DBU (2 mol % based on VDM) as catalyst. The bisacrylamide products were confirmed by IR and NMR spectroscopy.

EXAMPLES 19-22

Various polyols were reacted with 2-isopropenyl-4,4-dimethylazlactone (IDM) using the procedure of Example 2. The results are listed in Table 3.

TABLE 3

Methacrylamide Functional Compounds

| Example | Polyol | Refractive index | Viscosity (Poise, 30° C.) |
|---|---|---|---|
| 19 | Polypropylene glycol | 1.4688 | 22.5 |
| 20 | Placcel 305 | 1.4834 | 77.5 |
| 21 | PolyTMEG 650 | 1.4739 | 14.5 |
| 22 | Carbowax 600 | 1.4810 | 14.3 |

EXAMPLE 23

Cellulose acetate propionate (CAP ™ -504-0.2, available from Eastman Chemical Products, Inc., OH equiv wt 354) was dissolved in methyl ethyl ketone at 30% solids by weight. To this solution (49.16g) was added DBU (0.158 g), BHT (0.1 g), and VDM (5.79 g), and the reaction mixture was heated at 50° C. for 63 hrs. Analysis of the reaction mixture by IR indicated conversion to the acrylamide functional polymer.

EXAMPLE 24

A sulfonated polycaprolactone diol (OH equiv wt 835) was prepared according to U.S. Pat. No. 4,558,149 Example 1 (designated therein as "Sulfoester Polyol A"). This diol (428 g, 0.512 equiv), VDM (71.2 g 0.512 mol), BHT (0.43 g), and methyl ethyl ketone (166.4 g) were mixed to form a clear, light yellow solution. After addition of DBU (2.33 g 0.015 mol), the mixture was heated at 65° C. for 16 hrs. IR analysis of a coated film of the reaction solution showed no azlactone absorption bands and a spectrum consistent with the desired reaction product.

Similarly, the diol was reacted with IDM to produce the methacrylamide functional resin.

EXAMPLE 25

Glycerol (2.6 g, 0.085 equiv), VDM (11.78 g, 0.085 mol), DBU (1 drop), and methyl ethyl ketone (5 g) were combined in a dry vial, sealed, and placed in an oven at 60° C. After heating for 15 hrs, the reaction mixture was cooled to room temperature and the precipitated solid was filtered, washed with more solvent, and dried to give 8.4 g of a colorless solid. Spectral analysis verified that this compound was the trisacrylamide.

EXAMPLE 26

A mixture of polypropyleneglycol (OH equiv wt 380.9, 12.29 g, 32.3 mMol) and VDM (4.26 g, 30.6 mMol) was charged to a dry vial. The refractive index of this mixture was measured to be 1.4477. DBU (0.23 g, 1.53 mMol) was added, the vial sealed, and the contents thoroughly mixed. The refractive index was monitored periodically until it no longer showed any change (final value=1.4627). IR and NMR spectroscopy verified that the reaction was complete. The starting and final refractive indices were used to construct a graph of % conversion vs. refractive index, which could be used for the estimation of half-life for the reaction (see Table 4 below).

EXAMPLES 27-36

Various possible catalysts were evaluated using the other materials and procedure of Example 26. Half-lives were determined using the calibration curve developed in Example 26, and are reported in Table 4.

TABLE 4

Catalyst Evaluation

| Example | Catalyst[a] | pKa | Half life |
|---|---|---|---|
| 26 | DBU | 11.6 | 17 min |
| 27 | trioctylphosphine | 6.0 | less than 1 min |
| 28 | TBD | | less than 5 min |
| 29 | DBN | | 25 min |
| 30* | triethylamine | 10.75 | no reaction (9 days) |
| 31* | DMAP[b] | 9.7 | 335 hrs |
| 32* | proton sponge[c] | 12.3 | no reaction (7 days) |
| 33* | DABCO[d] | 8.6 | 935 hrs |
| 34* | 2-methylimidazoline | | no reaction (4 days) |
| 35* | TMG[e] | 13.9 | no reaction (4 days) |
| 36* | TMG/epoxide[f] | | no reaction (3 days) |

*comparative example
[a]All catalysts were used at 5 mole % based on VDM.
[b]4-dimethylaminopyridine.
[c]1,8-bis(dimethylamino)naphthalene.
[d]1,4-diazabicyclo[2.2.2]octane.
[e]1,1,3,3-Tetramethylguanidine.
[f]5 Mole % each of TMG and n-butyl glycidyl ether.

The data of Table 4 show that only the catalysts of Examples 26-29, within the present invention, gave useful reaction times.

EXAMPLE 37 (COMPARATIVE)

Example 26 was repeated substituting 2-ethyl-4,4-dimethylazlactone for VDM. The estimated half-life of the reaction was found to be 185 min, or approximately 11 times longer than that for reaction with VDM.

EXAMPLE 38

This example utilizes a phenoxy resin polyol (PKHH ™, available from Union Carbide Corp.) which possesses a hydroxy equivalent weight of 285. Reaction mixtures were prepared at 40% solids in tetrahydrofuran, and contained DBU (5 mol % based on VDM) and BHT (0.1% based on total wt of reactants). Four separate reactions were conducted, in which enough VDM was added to react with 20%, 40%, 60%, and 80% respectively of the hydroxy groups. The solutions were heated at 60° C. for 18 hrs, at which time IR analysis of the mixtures showed complete reaction of the azlactone.

EXAMPLE 39

The reaction of VDM and a perfluorinated polyether diol (Example 8 of U.S. Pat. No. 3,810,874) having a hydroxy equivalent weight of 1030 was conducted as follows:

The diol (28.94 g, 0.028 equiv) and VDM (3.98 g, 0.028 mol) were mixed to form a colorless solution. Upon addition of DBU (0.21 g, 0.0014 mol), a mildly exothermic reaction took place. After one hour, IR analysis showed complete conversion to the bisacrylamide.

EXAMPLE 40

Example 39 was repeated, except that IDM was used in place of VDM. IR analysis after one hour reaction time confirmed the formation of the bismethacrylamide.

EXAMPLE 41

To a solution of VDM (3.48 g, 25 mMol) and polypropylene glycol (OH equiv. wt. 190, 4.75 g, 25 mequiv.) was added trioctylphosphine (TOP, 0.46 g, 1.25 mMol, 5 mole % based on VDM). A rapid exotherm occurred which lasted for about 10 minutes. IR analysis of the viscous oil product after 30 minutes showed complete conversion to the bisacrylamide.

EXAMPLE 42

Example 41 was repeated substituting triethylphosphine for TOP. The reaction was complete within 23 minutes.

EXAMPLE 43

Reaction 41 was repeated substituting dimethylphenylphosphine for TOP. The reaction was complete within 23 minutes.

EXAMPLE 44

Reaction 41 was repeated substituting diphenylmethylphosphine for TOP. No exotherm was noted, however IR analysis after 24 hrs. indicated complete reaction.

EXAMPLE 45

Example 41 was repeated substituting tri-t-butylphosphine for TOP. A modest exotherm was observed. IR analysis after 24 hrs. indicated about 40% conversion to the acrylamide product.

EXAMPLE 46

Example 41 was repeated substituting triphenylphosphine for TOP and conducting the reaction at 65° C. NMR analysis after 24 hrs indicated 23% conversion to the acrylamide.

EXAMPLE 47

Example 46 was repeated utilizing triethylphosphite the catalyst. NMR analysis of the mixture after 24 hrs. indicated 23% conversion to the acrylamide.

EXAMPLE 48 (COMPARATIVE)

Example 46 was repeated utilizing trioctylphosphine oxide as the catalyst. No reaction was observed after 24 hrs.

EXAMPLE 49

Example 41 was repeated, substituting 1-phenyl-2-propanol for the polypropylene glycol. The reaction was strongly exothermic. NMR analysis of the product showed exclusive and complete ring-opening of the azlactone to produce the acrylamidoester.

EXAMPLE 50

Example 50 was repeated substituting IDM for VDM. The reaction was mildly exothermic. IR analysis of the product after 20 hrs. indicated complete conversion to the methacrylamide.

EXAMPLE 51 (COMPARATIVE)

Example 50 was repeated substituting 2-ethyl-4,4-dimethylazlactone for VDM. IR analysis after 20 hrs. showed less than 3% reaction had occurred.

EXAMPLE 52

TOP (0.26 g, 0.7 mMol) was added to a solution of VDM (1.95 g, 14 mMol), nitrocellulose (47.67 g of a 25.7% solids solution in methyl ethyl ketone, 35 mequiv. of OH), BHT (0.004 g) and methyl ethyl ketone (7.18 g). The solution was heated at 65° C. for 5 days. IR confirmed the formation of the acrylamide functional polymer. This solution can be utilized as a UV curable wood protective finish.

Various modifications and alterations of this invention will become apparent to those skilled in the art without departing from the scope and spirit of this invention, and it should be understood that this invention is not to be unduly limited to the illustrative embodiments set forth herein.

We claim:

1. A process comprising the steps of
   (a) reacting an alkenyl azlactone, a hydroxy functional compound, and a catalytically effective amount of a bicyclic amidine or a trivalent phosphorus compound, and
   (b) isolating the resulting acrylamide or methacrylamide functional monomer, oligomer, or polymer.

2. A process for preparing an acrylamide functional compound having the formula $$R\text{-}(OH)_{n-p}A_p$$

wherein
   R represents a monomeric, oligomeric, or polymeric organic group containing hydroxyl functionality, said group having a valence of n and a number average molecular weight of up to 5,000,000;
   n is a positive integer of at least one and represents the valence of R;
   p is a positive integer between 1 and n inclusively; and
   A is an acrylamide group having the formula $$CH_2=\overset{R^1}{\underset{}{C}}-\overset{O}{\underset{}{\overset{\|}{C}}}NHR^2\overset{R^3}{\underset{R^4}{\overset{|}{C}}}-\overset{O}{\underset{}{\overset{\|}{C}}}O-$$

wherein
   $R^1$ is hydrogen or methyl;
   $R^2$ is a single bond or $R^2$ is a methylene group which can be substituted by one or two alkyl groups having 1 to 6 carbon atoms or a phenyl group; and
   $R^3$ and $R^4$ are independently hydrogen, an alkyl group to 20 carbon atoms, a cycloalkyl group of 3 to 20 carbon atoms, an aryl group of 5 to 12 ring atoms, or an arenyl group of 6 to 26 carbon and heteroatoms, or $R^3$ and $R^4$ taken together with the carbon atom to which they are joined form a carbocyclic ring of 4 to 12 ring atoms, said process comprising the step of
   (a) reacting
   (1) a hydroxy functional compound having the formula $$R\text{-}(OH)_n$$

wherein
   R and n are as defined above,
   (2) one to n equivalents of an alkenyl azlactone of general Formula II:

$$\underset{CH_2=\overset{R^1}{\underset{}{C}}-C}{}\overset{N-R^2}{\underset{O-C}{\overset{\diagup}{\diagdown}}}\overset{R^3}{\underset{R^4}{\overset{\diagdown}{\diagup}}}C\quad\quad II$$

wherein
   n, $R^1$, $R^2$, $R^3$, $R^4$ are as defined above, and (3) an effective amount of a catalyst selected from the group consisting of (a) bicyclic amidines and (b) trivalent phosphorus compounds, to produce said acrylamide functional compound.

3. The process according to claim 2 wherein R is derived from the group consisting of monomeric, oligomeric and polymeric alcohols.

4. The process according to claim 3 wherein said alcohol is selected from the group consisting of polyether polyols, polyester polyols, polysiloxane polyols, polycarbonate polyols, hydroxy functional polyacrylic and polymethacrylic ester polymers, phenolic resins, polymers and copolymers of hydroxy functional vinyl monomers, polymers and copolymers of vinyl esters, cellulose and modified cellulose polymers, and phenoxy polymers.

5. The process according to claim 2 wherein said azlactone is selected from the group selected from
4,4-dimethyl-2-ethenyl-2-oxazolin-5-one,
4,4-dimethyl-2-isopropenyl-2-oxazolin-5-one,
2-ethenyl-4-methyl-4-phenyl-2-oxazolin-5-one,
2-ethenyl-4,4-pentamethylene-2-oxazolin-5-one,
4,4-diphenyl-2-isopropenyl-2-oxazolin-5-one,
2-ethenyl-4-ethyl-4-methyl-2-oxazolin-5-one, and
4,4-dimethyl-2-ethenyl-4,5-dihydro-1,3-oxazin-6-one.

6. The process according to claim 2 wherein said bicyclic amidine has the formula

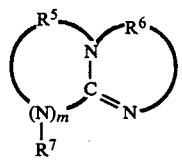

wherein
$R^5$ and $R^6$ independently are alkylene groups of 2 to 12 carbon atoms,
$R^7$ is an alkyl group of 1 to 20 carbon atoms or aryl group of 5 to 12 ring atoms containing up to 3 S, N, and O atoms, and
m is 0 or 1.

7. The process according to claim 6 wherein at least one of said $R^5$ and $R^6$ alkylene groups are substituted by at least one aryl group having 5 to 12 ring atoms containing up to 3 S, N, and O atoms, or by at least one alkyl group having 1 to 20 carbon atoms.

8. The process according to claim 6 wherein said $R^7$ aryl group is substituted by one to three atoms and groups selected from the group consisting of halogen atoms, lower alkyl groups, lower alkoxy groups, N,N-di (lower alkyl) amino, nitro, cyano, and lower alkyl carboxylic ester groups, wherein lower is $C_1$ to $C_4$.

9. The process according to claim 2 wherein said trivalent phosphorus compound has the formula

wherein $R^8$, $R^9$, and $R^{10}$ independently are selected from the group consisting of H, an alkyl group having 1 to 20 carbon atoms, an aryl group having 5 to 12 ring atoms and up to 3 S, N, and O heteroatoms, an arenyl group having 6 to 26 carbon atoms and up to 3 S, N, and O heteroatoms, a lower alkoxy group having 1 to 4 C atoms, and a lower dialkyl amino group having 2 to 8 C atoms.

10. The process according to claim 6 wherein said bicyclic amidine is selected from the group consisting of
1,5-diazabicyclo[4.3.0]non-5-ene,
1,8-diazabicyclo[5.4.0]undec-7-ene, and
1,5,7-triazabicyclo[4.4.0]dec-5-ene.

11. The process according to claim 9 wherein said trivalent phosphorus compound is selected from the group consisting of trimethylphosphine, triethylphosphine, triethylphosphite, tributylphosphine, trioctylphosphine, dimethylphenylphosphine, diphenylmethylphosphine, diphenylphosphine, dipropylphosphine, tris(dimethylamino)phosphine, 1,2-bis(di-n-propylphosphine)ethane, 1,3-bis(diphenylphosphine)propane, diethylmethoxyphosphine, and triphenylphosphine.

12. The process according to claim 2 wherein said catalyst is present in an amount in the range of 0.1 mole percent to 50 mole percent based on azlactone.

13. The process according to claim 2 wherein said catalyst is polymer bound.

14. The process according to claim 2 wherein said reaction takes place in the temperature range of 0° C. to 100° C.

15. The process according to claim 2 further comprising a nonreactive solvent or diluent.

16. The process according to claim 2 further comprising an effective amount of an antioxidant or a free radical inhibitor.

17. The process according to claim 2 further comprising the step of curing the resulting acrylamide or methacrylamide functional compound.

18. The process according to claim 2 for preparing a curable resin.

19. The process according to claim 17 for preparing a cured resin.

20. A composition of matter comprising
(a) an acrylamide functional compound having the formula

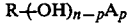

wherein
R represents a monomeric, oligomeric, or polymeric organic group containing hydroxyl functionality, said group having a valence of n and a number average molecular weight of up to 5,000,000;
n is a positive integer of at least one and repesents the valence of R;
p is a positive integer between 1 and n inclusively; and
A is an acrylamide group having the formula

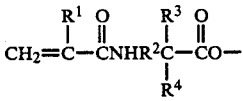

wherein
$R^1$ is hydrogen or methyl;
$R^2$ is single bond or $R^2$ is methylene group which can be substituted by one or two alkyl groups having 1 to 6 carbon atoms or a phenyl group; and
$R^3$ and $R^4$ are independently hydrogen, an alkyl group of 1 to 20 carbon atoms, a cycloalkyl group of 3 to 20 carbon atoms, an aryl group of 5 to 12 ring atoms, or an arenyl group of 6 to 26 carbon and heteroatoms, or $R^3$ and $R^4$ taken together with the carbon atoms to which they are joined form a carbocyclic ring of 4 to 12 ring atoms, and (b) a catalytically effective amount of a bicyclic amidine or a trivalent phosphorus compound.

21. The process according to claim 1 wherein said alkenyl azlactone is 2-vinyl-4,4-dimethylazlactone, said hydroxy functional compound is polycaprolactone polyol, and said bicyclic amidine is 1,5-diazabicyclo non-5-ene.

22. A process comprising the step of reacting an alkenyl azlactone, a hydroxy functional compound, and a catalytically effective amount of a bicyclic amidine or a trivalent phosphorus compound, to provide an acrylamide or methacrylamide functional monomer, oligomer, or polymer.

* * * * *

UNITED STATES PATENT AND TRADEMARK OFFICE
CERTIFICATE OF CORRECTION

PATENT NO. : 4,874,822

DATED : October 17, 1989

INVENTOR(S) : Jerald K. Rasmussen et al.

It is certified that error appears in the above-identified patent and that said Letters Patent is hereby corrected as shown below:

Col. 2, line 22, "a DBU" should read -- as DBU --.

Col. 7, line 35, after the word "of", kindly insert -- some of the --.

Col. 12, line 42, after the word "group" kindly insert -- of 1 --.

Col. 16, lines 1-2, "1,5-diazabicyclo non-5-ene" should read -- 1,5-diazabicyclo[4.3.0]non-5-ene --.

Signed and Sealed this

Tenth Day of March, 1992

Attest:

HARRY F. MANBECK, JR.

Attesting Officer

Commissioner of Patents and Trademarks